United States Patent [19]

Sofia

[11] Patent Number: 5,055,489
[45] Date of Patent: Oct. 8, 1991

[54] METHOD FOR THE PREVENTION AND CONTROL OF HYPOXIC DAMAGE RESULTING FROM CEREBRAL ISCHEMIC EVENTS

[75] Inventor: Robert D. Sofia, Willingboro, N.J.

[73] Assignee: Carter-Wallace, Inc., New York, N.Y.

[21] Appl. No.: 518,892

[22] Filed: May 4, 1990

[51] Int. Cl.$^5$ .................. A61K 31/27; A61K 31/135; A61K 31/13

[52] U.S. Cl. .................................. 514/483; 514/649; 514/659

[58] Field of Search ........................ 514/483, 649, 659

Primary Examiner—Stanley J. Friedman
Assistant Examiner—Terry Wilson
Attorney, Agent, or Firm—Kevin B. Clarke

[57] ABSTRACT

A method for the prevention and control of hypoxic damage resulting from stroke or other cerebral ischemic event which comprises administering pharmaceutical compositions containing 2-phenyl-1, 3-propanediol dicarbamate as an active ingredient.

1 Claim, No Drawings

METHOD FOR THE PREVENTION AND CONTROL OF HYPOXIC DAMAGE RESULTING FROM CEREBRAL ISCHEMIC EVENTS

The present invention relates to pharmaceutical compositions containing 2-phenyl-1,3-propanediol dicarbamate as an active component and to methods for the prevention and control of hypoxic damage resulting from stroke or other ischemic event through the use of such compositions.

More particularly, the present invention relates to methods for protecting against hypoxic damage resulting from stroke and other cerebral ischemic events through the administration of therapeutic compositions which contain as an active ingredient 2-phenyl-1,3-propanediol dicarbamate, commonly known as Felbamate.

Felbamate is a well known pharmaceutical compound having been described together with methods for its manufacture in U.S. Pat. Nos. 2,884,444 and 4,868,327.

One of the objects of the present invention is to provide compositions for the prevention and control of hypoxic damage.

Another object of the present invention is to provide relatively non-toxic compositions effective to control or prevent hypoxic damage resulting from stroke or other cerebral ischemic event which include felbamate as an active component.

A further object of the present invention is to provide compositions for the prevention and control of hypoxic damage which compositions are relatively non-toxic, have a high degree of effectiveness and continue to produce a therapeutic response over relatively long periods of time.

Moreover, it is an object of the present invention to provide methods for the prevention and control of hypoxic damage through the use of felbamate.

Accordingly, it has been found that felbamate chemically described as 2-phenyl-1,3-propanediol dicarbamate is a compound which has demonstrated superior properties with respect to controlling and/or preventing hypoxic damage resulting from stroke or other ischemic cerebral event.

The neuro-protective effects of felbamate against hypoxic damage were investigated in the hippocampal slice model as described in the following example. This in vitro model simulates in vivo hypoxic-ischemic neuronal insults such as occur in stroke and other cerebral ischemic events.

EXAMPLE I

Sprague-Dawley rats are briefly anesthetized with Halothane and then decapitated. The brain is removed and the hippocampus dissected. Transverse hippocampal brain slices of 475 microns are sectioned with a McIlwain tissue chopper. Slices are then incubated in a temperature controlled chamber of 34 degrees centigrade while being perfused with an artificial cerebral spinal fluid (NaCl 126 mM; KCl, 4; $KH_2PO_4$, 1.4; $MgSO_4$, 1.3; $CaCl_2$, 2.4; $NaHCO_3$, 26 and glucose, 4) saturated with 95% $O_2$ and 5% $CO_2$.

After an initial one hour equilibration period, the slices are tested for electrophysiological function. Electrical stimulation is given in the region of the CA3 collaterals with a bipolar twisted wire electrode. Evoked responses are recorded extracellularly in the pyramidal cell layer of the CA1 region. Stimulation is given for a duration of 40 microseconds in square wave pulses. The peak-to-peak amplitude of the resultant evoked potential response is then monitored.

Hippocampal slices from one animal are placed in two chambers. One chamber is used as a control and receives standard artificial cerebral spinal fluid (ACSF) while the second receives felbamate. In each chamber, one slice is stimulated every 30 seconds to monitor evoked potential response. Other slices in the chamber are not continuously stimulated. In these latter slices, designated as non-stimulated, the evoked potential response is assessed only at the beginning and end of the experiment. Only slices with initial evoked potentials of 3 mV or greater amplitude are included for testing.

The experimental chamber is perfused with oxygenated artificial cerebral spinal fluid (ACSF) containing felbamate for 30 minutes before the initiation of hypoxic conditions. The control chamber continues to receive oxygenated ACSF without felbamate during this period. Hypoxic conditions are then initiated simultaneously in both chambers by changing to perfusing media saturated with 95% $N_2$ and 5% $CO_2$. The experimental chamber receives nitrogenated ACSF with felbamate while the control chamber receives nitrogenated ACSF without felbamate.

The duration of hypoxic exposure for both chambers is determined by the disappearance of the hypoxic injury potential (HIP) in the control stimulated slice. This potential appears during hypoxia after the disappearance of the original evoked potential. Although hippocampal slices can vary in their temporal response to hypoxia, the HIP is a reliable marker of permanent hypoxic injury. For this reason, the disappearance of the HIP is chosen to determine length of hypoxic exposure. Hypoxia is continued in both chambers for 5 minutes beyond the disappearance of the HIP in the stimulated control slice.

After hypoxic exposure, slices are monitored through one hour of recovery with oxygenated ACSF. The felbamate chamber receives oxygenated ACSF with felbamate for the first 15 minutes of this recovery and then standard oxygenated ACSF for the remaining 45 minutes of recovery. After a one-hour recovery period, the percentage of evoked potential amplitude recovery is assessed in both stimulated and non-stimulated slices. This percentage is calculated as the evoked potential amplitude after recovery divided by the evoked potential amplitude prior to hypoxic exposure.

The results of the foregoing procedure are as follows:

a. Pre-hypoxic Incubation.

Felbamate perfusion produced occasional transient collapse and disappearance of the evoked potential, but no evidence of toxicity as evidenced by permanent potential loss was seen.

b. Hypoxic Neuro-protection.

Significant neuro-protection against hypoxia is seen at felbamate concentrations of 380 uM, 840 uM, 1,300 uM and 1,700 uM.

This protective action is assessed by several measures. First, evoked potential recovery is assessed in both stimulated and non-stimulated slices. Additionally, hypoxic protection is calculated for both stimulated and non-stimulated slices. This measure is calculated as the damage seen in control slices minus the damage seen in experimental (felbamate) slices divided by the damage seen in control slices. For these purposes damage is defined as 100 percent minus percent recovery. The determination of hypoxic protection helps take into account any survival seen in control slices. Lastly, counts of total surviving slices were made. For this purpose a minimal amplitude criteria of 3 mV was used as the indicator of a surviving slice.

In stimulated control slices, hypoxic exposure resulted in near complete loss (1.0% mean recovery) of the population spike, while slices treated with 4, 190, 380, 840, 1,300 and 1,700 uM felbamate showed respectively 2%, 6%, 13%, 46%, 95% and 96% recovery. This recovery is significant at p 0.05 for 840 uM and significant at p 0.001 for concentrations of 1,300 and 1,700 uM. Since recovery in the stimulated control slices is minimal, calculated protection was essentially identical to recovery. Counts of surviving stimulated slices indicated substantial felbamate protection at doses of 1,300 and 1,700 uM. Interestingly, 1,700 uM felbamate delayed the appearance of the HIP by 14.5 minutes (p 0.05) but did not affect the disappearance of the evoked potential.

In non-stimulated control slices, recovery from hypoxic exposure shows greater recovery than stimulated control slices and a mean non-stimulated control recovery of 30% is seen. Calculated protection with felbamate concentrations of 4, 190, 380, 840, 1,300 and 1,700 uM, show respective values of 4%, 63%, 48%, 100% and 100%. Additionally, counts of surviving non-stimulated slices showed substantial protection.

The foregoing example indicates a significant hypoxic neuro-protective effect with felbamate within a wide concentration range (380 to 1,700 uM) in the hippocampal slice hypoxic model. Felbamate's hypoxic $EC_{50}$ in vitro appears to fall between its anticonvulsant $ED_{50}$ for MES (46 mg/kg) and metrazol (238 mg/kg) in rats. At high concentration of felbamate, no evidence of toxicity for electrophysiological function is seen.

The compositions of the present invention may take any of a variety of forms although they are intended primarily for oral use and are suitable for forming into pills, capsules and tablets by well-known practices.

When the active ingredient is in the form of a solid, a typical tablet composition comprises 2-phenyl-1,3-propanediol dicarbamate intermixed in a dry pulverulent state with suitable solid carriers and diluents.

Solid carriers and diluents suitable for use include sugars such as lactose and sucrose; cellulose derivatives such as carboxymethyl cellulose, ethyl cellulose, methyl cellulose, etc., gelatin including hard and soft gelatin capsules, talc, cornstarch, stearic acid and magnesium stearate.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets.

Felbamate (2-phenyl-1,3-propanediol dicarbamate) has a very favorable preclinical profile characterized by a substantial margin of safety (protective index 16.9–19.1).

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for the prevention and treatment of hypoxic damage following a stroke or other cerebral ischemic events in human or other warm-blooded animal patient which comprises administering to said patient in need of such treatment 2-phenyl-1,3-propanediol dicarbamate.

* * * * *